US010182754B2

(12) United States Patent
Mendels et al.

(10) Patent No.: US 10,182,754 B2
(45) Date of Patent: Jan. 22, 2019

(54) IN LINE FLUID SAMPLING PORT

(71) Applicant: BIOMETRIX LTD., Jerusalem (IL)

(72) Inventors: Yair Mendels, Moza Elit (IL); Matan Shamir, Jerusalem (IL)

(73) Assignee: BIOMETRIX LTD., Jerusalem (IL)

( * ) Notice: Subject to any disclaimer, the term of this patent is extended or adjusted under 35 U.S.C. 154(b) by 684 days.

(21) Appl. No.: 14/766,861

(22) PCT Filed: Jan. 17, 2014

(86) PCT No.: PCT/US2014/011966
§ 371 (c)(1),
(2) Date: Aug. 10, 2015

(87) PCT Pub. No.: WO2014/123678
PCT Pub. Date: Aug. 14, 2014

(65) Prior Publication Data
US 2016/0000364 A1    Jan. 7, 2016

Related U.S. Application Data

(60) Provisional application No. 61/763,208, filed on Feb. 11, 2013.

(51) Int. Cl.
*A61B 5/15* (2006.01)
*A61M 39/02* (2006.01)

(52) U.S. Cl.
CPC .... *A61B 5/150992* (2013.01); *A61B 5/15003* (2013.01); *A61B 5/150221* (2013.01); *A61M 39/02* (2013.01); *A61M 2039/0202* (2013.01)

(58) Field of Classification Search
CPC .................... A61M 39/06; A61B 5/150992
See application file for complete search history.

(56) References Cited

U.S. PATENT DOCUMENTS

| 5,441,487 | A   | * | 8/1995  | Vedder  | A61M 39/045 |
|           |     |   |         |         | 604/167.03  |
| 6,855,138 | B2  | * | 2/2005  | Tsai    | A61M 39/26  |
|           |     |   |         |         | 604/537     |
| 7,972,322 | B2  |   | 7/2011  | Tennican |            |
| 2005/0261637 | A1 | * | 11/2005 | Miller | A61M 39/045 |
|           |     |   |         |         | 604/256     |

FOREIGN PATENT DOCUMENTS

WO            9500188        1/1995

OTHER PUBLICATIONS

International Search Report dated Mar. 31, 2014 for PCT/US2014/011966, filed Jan. 17, 2014.
International Preliminary Report on Patentability with Written Opinion, dated Aug. 11, 2015, for PCT/US2014/011966.

* cited by examiner

*Primary Examiner* — Daniel L Cerioni
*Assistant Examiner* — Yasmeen S Warsi
(74) *Attorney, Agent, or Firm* — Paul D. Bianco; Gary S. Winer; Fleit Gibbons Gutman Bongini & Bianco PL

(57) ABSTRACT

A fluid sampling ports for withdrawing and administering fluids from or to a sampling site. The sampling valve is interconnected in a line to and/or from a patient with the line carrying a fluid that one wishes to sample. In a particular example, the sampling valve or port is interconnected in an arterial line and/or serves as a dialysis fluid sampling port.

19 Claims, 9 Drawing Sheets

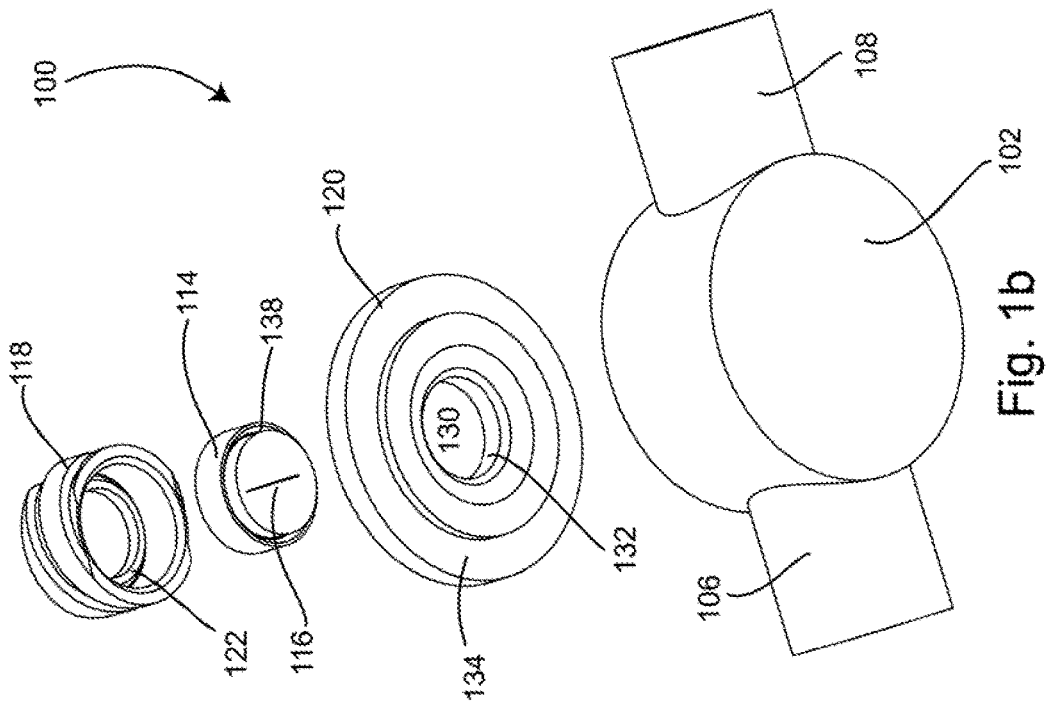
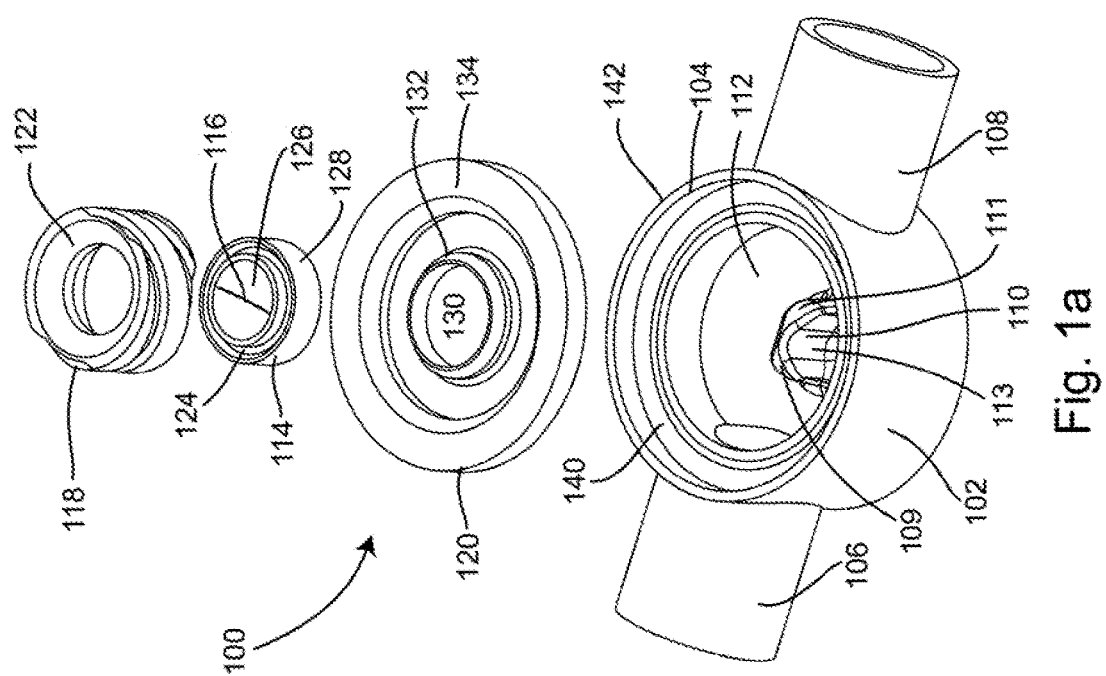

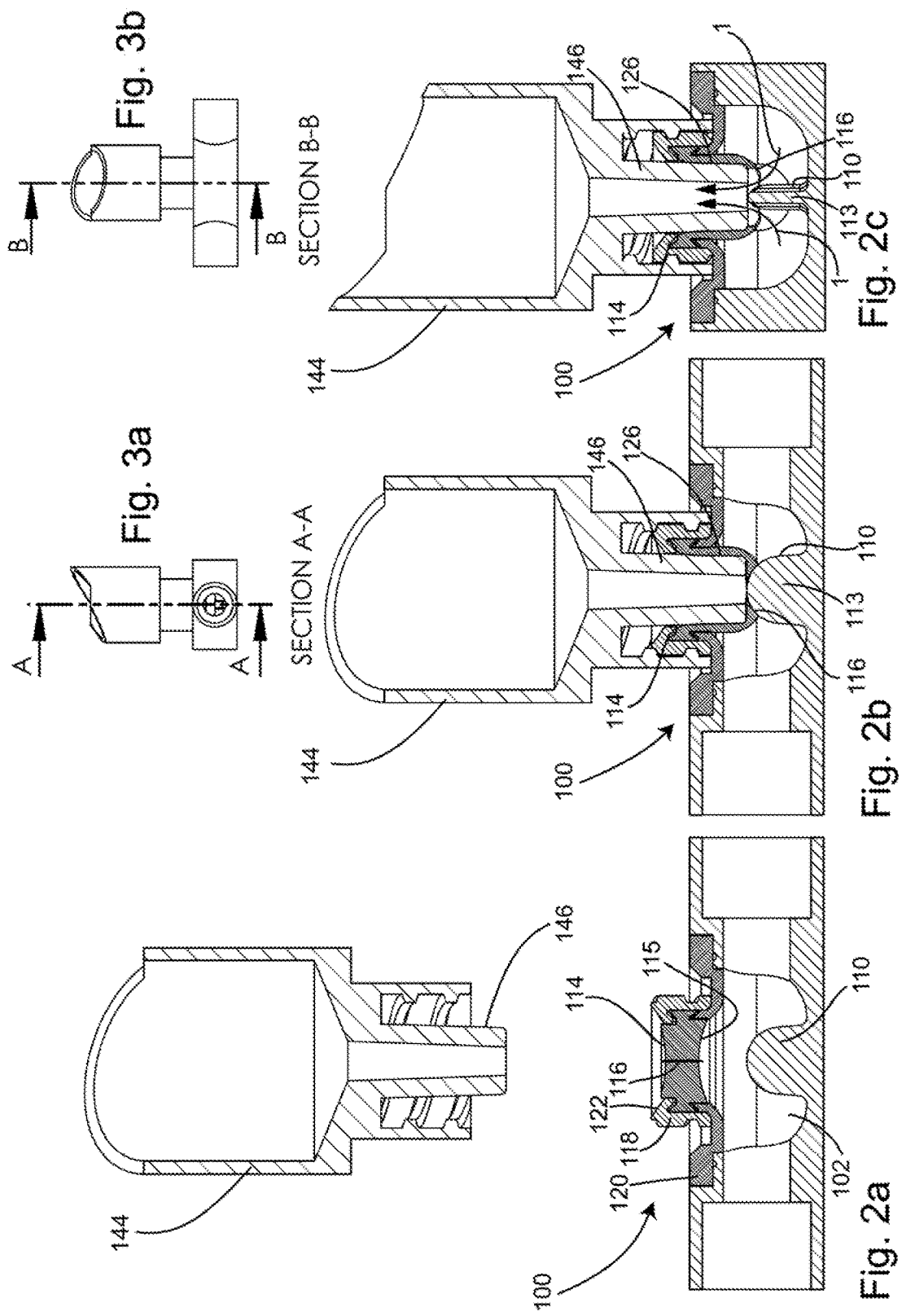

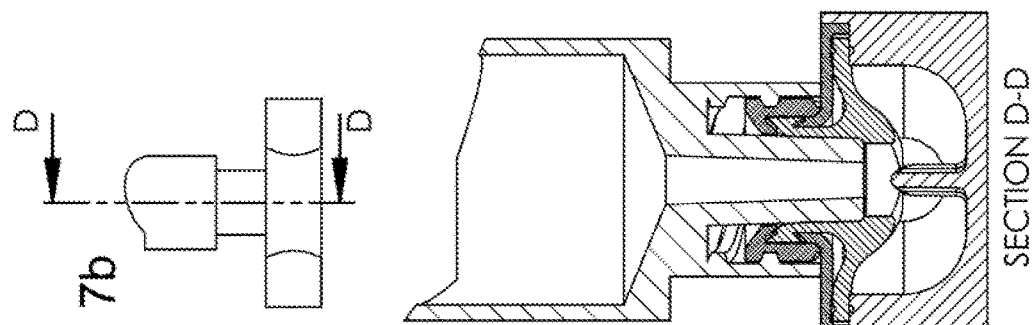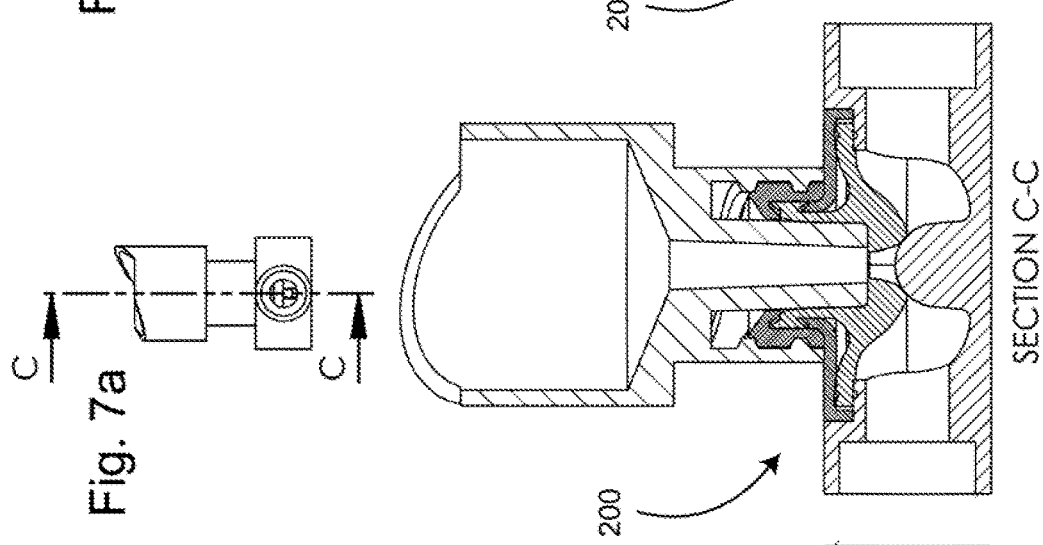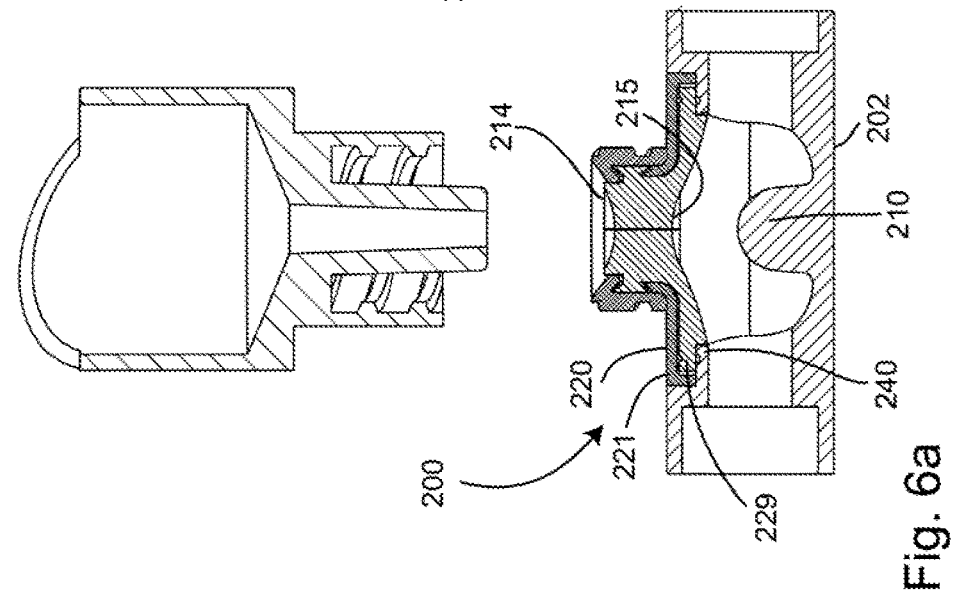

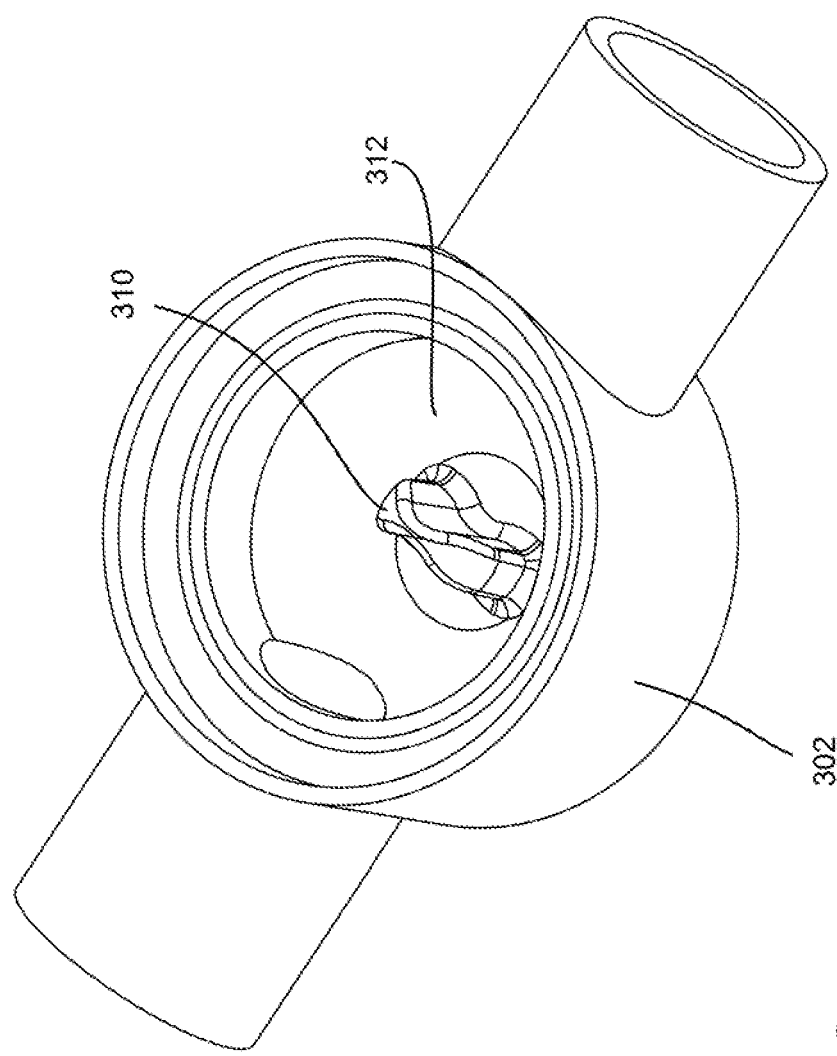

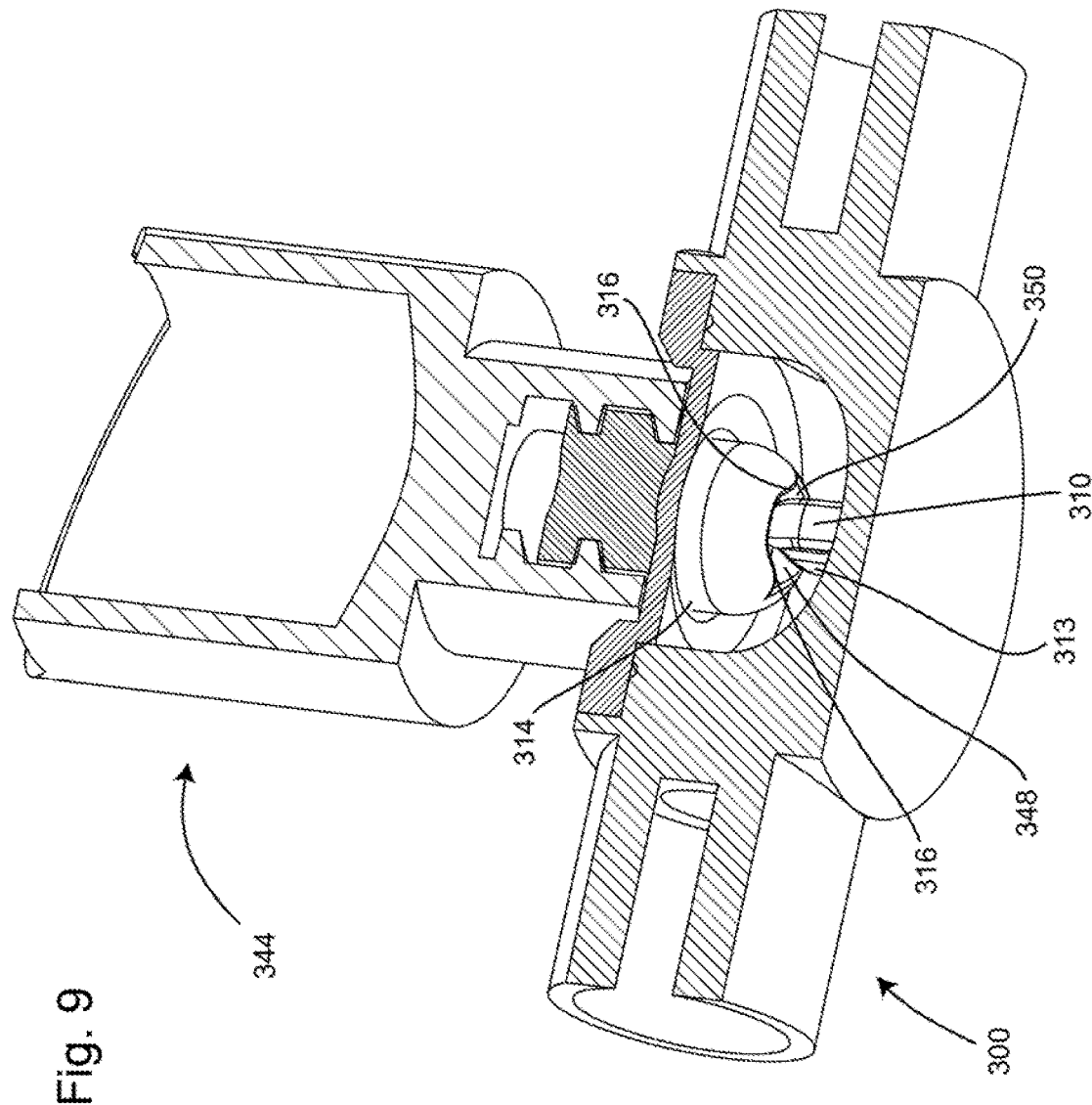

IN LINE FLUID SAMPLING PORT

FIELD OF THE INVENTION

The present invention relates to the field of fluid sampling ports. Particularly, the present invention relates to apparatus and a method for withdrawing and administering fluids from or to a sampling site. A sampling valve is provided that is interconnected in a line to and/or from a patient with the line carrying a fluid that one wishes to sample. More particularly the present invention relates to arterial line and dialysis fluid sampling ports.

SUMMARY OF THE INVENTION

In accordance with a preferred embodiment of the present invention, a fluid sampling port is disclosed, comprising a receptacle having an open portion, an inlet and an outlet, and a sampling valve held in position at the open portion by securing members, whereby the valve and the securing members together seal the open portion. The receptacle further comprises a valve separator extending from its surface toward the valve.

Preferably, the securing members comprise a rigid cylindrical element for positioning around the valve, and a rigid disc element for supporting the valve. The valve is preferably threadingly engaged with the securing members. The rigid cylindrical element is preferably externally threaded for mating with a needle-less connector.

Optionally, the valve separator is longitudinally oriented along the direction of fluid flow through the receptacle. Alternatively, the valve separator is longitudinally oriented orthogonal to the direction of fluid flow through the receptacle.

The slit of the valve is preferably oriented orthogonal to the longitudinal axis of the valve separator.

The valve separator preferably comprises a figure-eight cross-sectional shape when cut longitudinally, planar with the bottom surface of the receptacle, comprising wide ends and a narrow middle section.

Preferably, the valve slit separates upon contact with the valve separator. When the valve slit separates, a gap forms between the narrow middle section of the valve separator and the separated slit, through which a sampling fluid may be drawn.

BRIEF DESCRIPTION OF THE FIGURES

FIGS. 2*a-c* show a cross-sectional side view of the assembled first embodiment of the sampling port cut longitudinally, with a male luer connector spaced apart from sampling port (FIG. 2*a*), mated with sampling port (FIG. 2*b*) and cut transversely mated with sampling port (FIG. 2*c*);

FIGS. 3*a-b* show the longitudinal cut line of FIGS. 2*a-b* (FIG. 3*a*) and the transverse cut line of FIG. 2*c* (FIG. 3*b*);

FIGS. 6*a-c* show a cross-sectional side view of the assembled second embodiment of the sampling port cut longitudinally with a male luer connector spaced apart from sampling port (FIG. 6*a*), mated with sampling port (FIG. 6*b*) and cut transversely mated with sampling port (FIG. 6*c*);

FIGS. 7*a-b* show the longitudinal cut line of FIGS. 6*a-b* (FIG. 7*a*) and the transverse cut line of FIG. 6*c* (FIG. 7*b*);

FIG. 8 shows the receptacle portion of a third embodiment of the sampling port of the present invention with the valve separator oriented orthogonal to the direction of fluid flow through the receptacle; and, FIG. 9 shows a partially cut isometric view of the assembled sampling port of the third embodiment with a luer connector mated therewith.

DETAILED DESCRIPTION OF THE PREFERRED EMBODIMENTS

The term, "fluid" as used herein refers to any fluid, including bio-fluid, such as blood, etc., as well as disinfectant fluid, therapeutic fluid, etc.

Figure 1C:
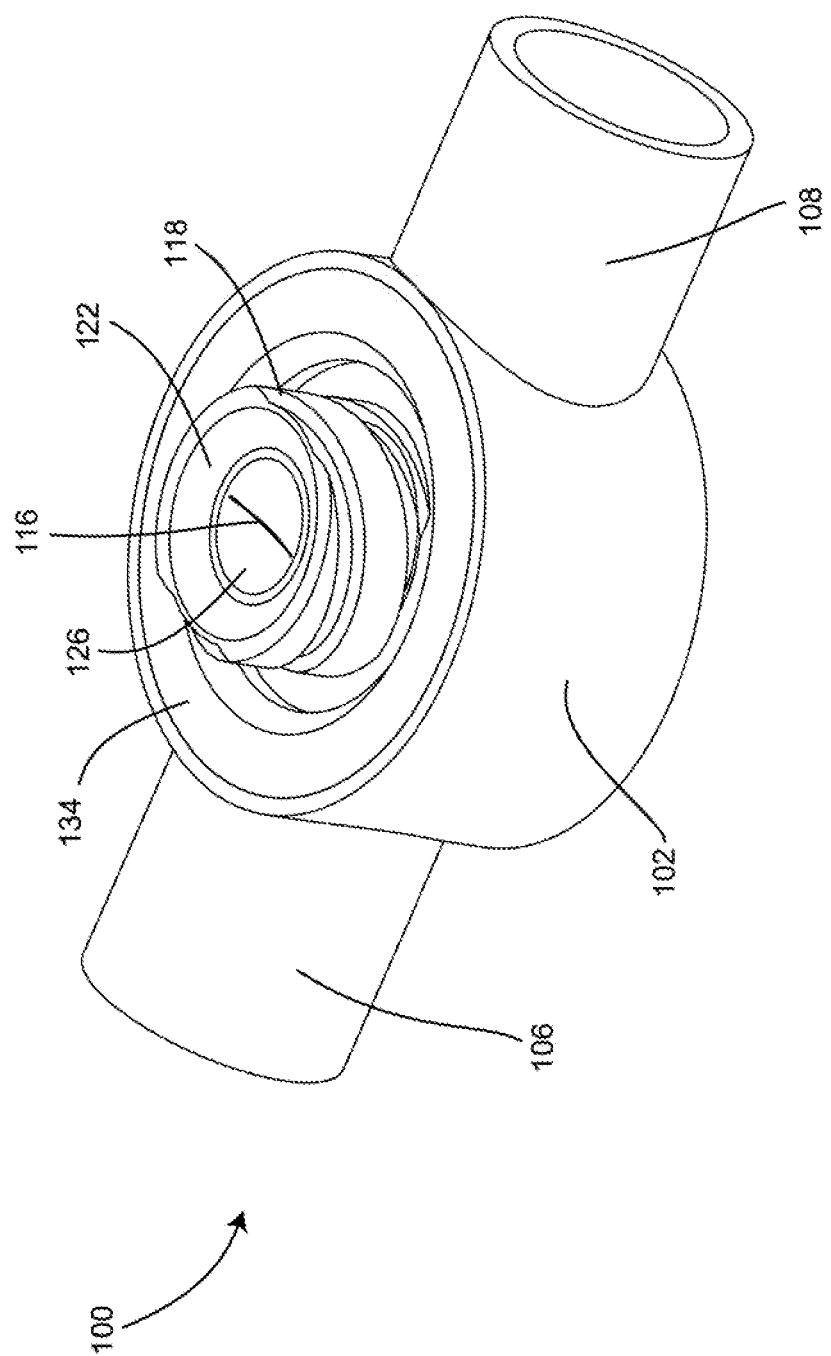
FIGS. 1 *a-c* show a first embodiment of the fluid sampling port of the present invention in an exploded top view (FIG. 1*a*), an exploded bottom view (FIG. 1*b*) and an isometric assembled view (FIG. 1*c*)

A first preferred embodiment of the fluid sampling port of the present invention is shown in FIGS. 1*a-c* in an exploded top view (FIG. 1*a*), an exploded bottom view (FIG. 1*b*) and an isometric assembled view (FIG. 1*c*), and is designated generally by numeral (100). Sampling port (100) comprises a receptacle (102) having an open portion (104), an inlet (106) and an outlet (108). A valve separator (110) extends from the bottom surface (112) of receptacle (102) toward the sampling valve (114) for separating the slit (116) of valve (114) when a needle-less (luer) connector is inserted, as described herein below. Valve separator (110) is longitudinally oriented along the direction of fluid flow through receptacle (102), i.e. from inlet (106) to outlet (108), and comprises a figure-eight cross-sectional shape when cut longitudinally, planar with the bottom surface (112) of receptacle (102), having wide ends (109), (111) and a narrow middle section (113). When assembled, valve (114) is positioned at open portion (104) of receptacle (102) and held in position by securing members (118) and (120). Securing member (118) comprises a rigid cylindrical element for surrounding valve (114), having an inwardly declining upper lip (122) disposed within the groove ring (124) formed at the upper portion of valve (114) between the slit segment (126) and the outer wall (128). The outer surface of securing member (118) is threaded for mating with the luer connector described herein below. Securing member (120) comprises a rigid disc element having a central opening (130) surrounded by a protruding neck (132), and a raised outer periphery (134). When assembled, neck (132) is disposed within the groove ring (138) formed at the lower portion of valve (114) between slit segment (126) and outer wall (128). Raised periphery (134) of member (120) is positioned on the inwardly extending lip (140) slightly beneath the upper rim (142) of receptacle (102).

Referring to FIGS. 2*a-c* and FIGS. 3*a-b*, the assembled sampling port (100) is shown assembled with a male luer connector (144) threadingly mated therewith, in a cross-sectional side view (FIG. 2*b*) cut longitudinally along A-A of FIG. 3*a*, and in a cross-sectional side view (FIG. 2*c*) and cut transversely along B-B of FIG. 3*b* (orthogonal to A-A of FIG. 3*a*). FIG. 2*a* shows the same cross-sectional cut as FIG. 2*b*, but with luer connector (144) spaced apart from sampling port (100). FIGS. 2*a-c* will now be described in further detail.

Figure 4:
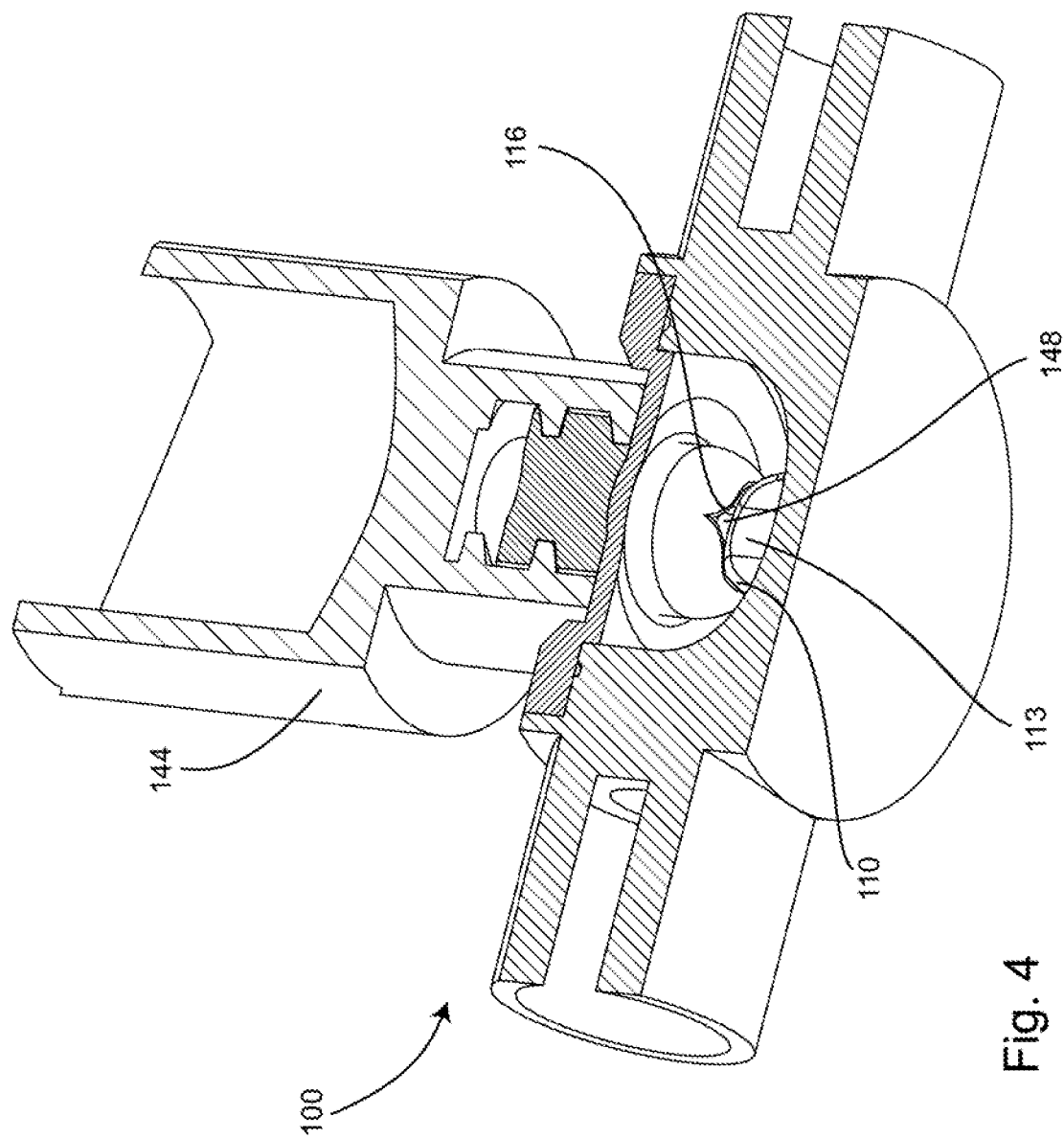
FIG. 4 shows a partially cut isometric view of the assembled sampling port with a luer connector mated therewith.

As best seen in FIG. 2*a* (as well as in FIG. 1*a*), slit (116) of valve (114) is oriented orthogonally to the longitudinal axis of valve separator (110). Referring to FIGS. 2b-c, when threadingly mating luer connector (144) with sampling port (100), male portion (146) of luer connector (144) presses slit segment (126) of valve (114) toward valve separator (110). Upon contact with valve separator (110), slit (116) of valve (114) separates, as shown in the figure. Each end of slit (116) is disposed over an opposing side of the narrow middle section (113) of valve separator (110), forming a gap between the separated opposing ends of slit (116) and valve separator (110) through which a sampling fluid may be drawn, as indicated by arrows (1) in FIG. 2c. This can be best seen in FIG. 4, showing a partially cut isometric view of assembled sampling port (100) with luer connector (144) mated therewith. Gap (148) is shown formed between one end of separated slit (116) and one side of the narrow middle section (113) of valve separator (110). An essentially identical gap is formed on the other side of narrow middle section (113) (not shown in the figures).

Figure 5B:
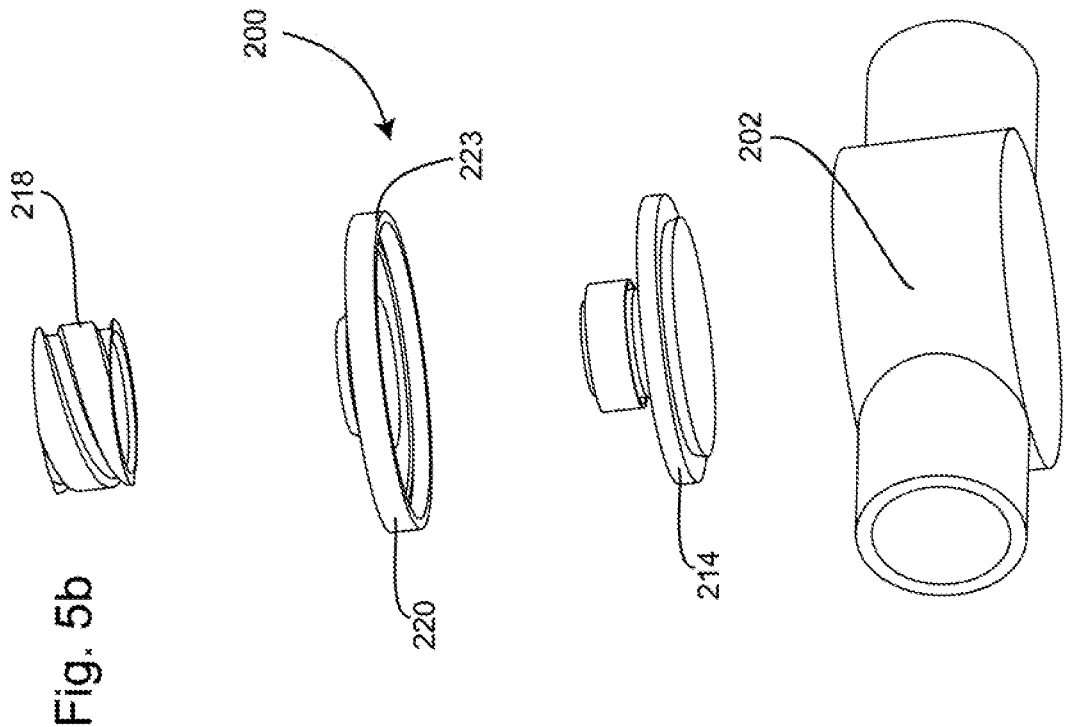
FIGS. 5*a-c* show a second embodiment of the fluid sampling port of the present invention in an exploded top view (FIG. 5*a*), an exploded bottom view (FIG. 5*b*) and an isometric assembled view (FIG. 5*c*)
Figure 5A:
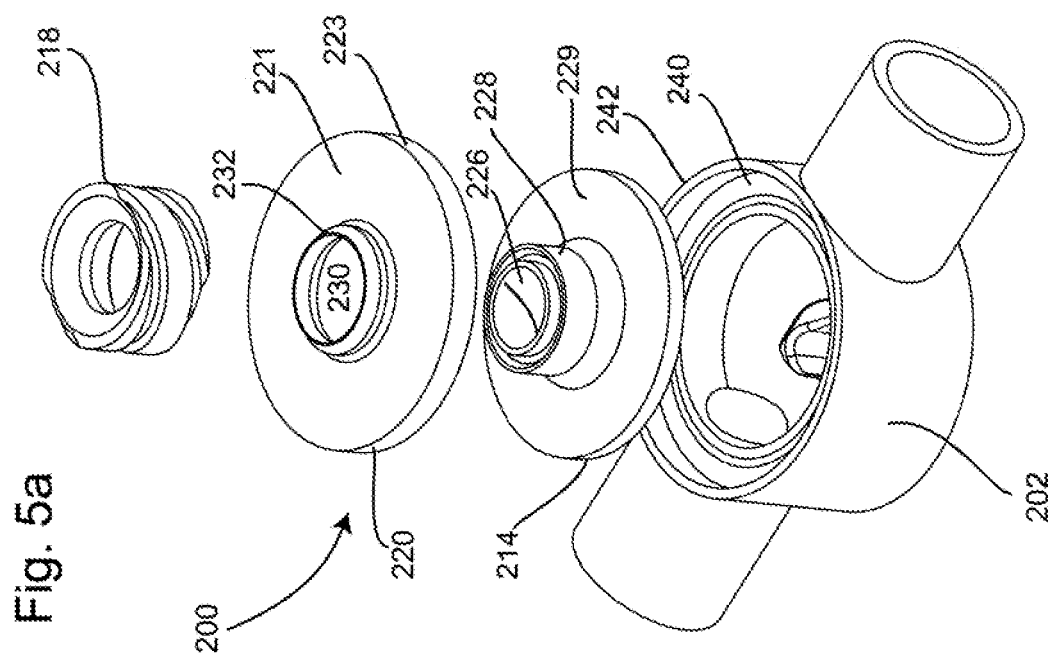
Figure 5C:
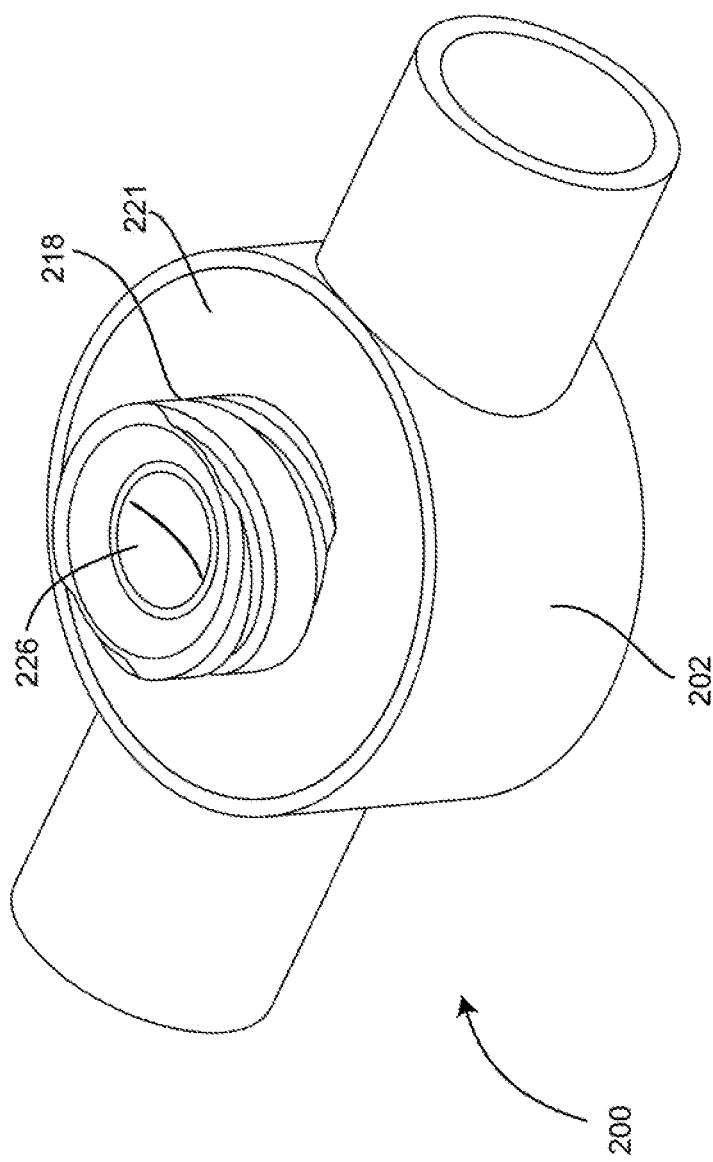

A second preferred embodiment of the fluid sampling port of the present invention is shown in FIGS. 5a-c in an exploded top view (FIG. 5a), an exploded bottom view (FIG. 5b) and an isometric assembled view (FIG. 5c), and is designated generally by numeral (200), comprising the same essential features and elements of sampling port (100) of the first embodiment, mutatis mutandis, with the following differences.

Valve (214) comprises a slit segment (226) and an outer wall (228) protruding from the center of flange (229). When assembled, the periphery of flange (229) is positioned on the inwardly extending lip (240) slightly beneath the upper rim (242) of receptacle (202).

Securing member (220) comprises a rigid disc (221) having a central opening (230) surrounded by a protruding neck (232). Disc (221) is positioned over flange (229) of valve (214). The outer edge (223) of disc (221) extends orthogonally toward lip (240), forming a ring surrounding flange (229).

FIGS. 6a-c show sampling port (200) in the same views as that shown in FIGS. 2a-c of the first embodiment of sampling port (100), as cut along the lines indicated in FIGS. 6a-b, mutatis mutandis. The main difference between the second embodiment of sampling port (200) and the first embodiment of sampling port (100) can be best seen in FIG. 6a. The lower contour (215) of valve (214) is shown shaped as a crest of a wave having a long wavelength and short amplitude. This design overcomes a drawback associated with prior art sampling port valves whose lower contour is shaped as a crest of a wave having a short wavelength and high amplitude. In the prior art design, therefore, fluid becomes trapped in the pocket formed by the contour of the valve. This fluid is difficult to wash away by the fluid that flows through the port. Consequently, the fluid sampling that is withdrawn is "old" fluid from the pocket, rather than "new" fluid obtained from continuous fluid flow through the port. This may effect the results from the fluid sample analysis. In contrast, contour (215) is designed to avoid collection of fluid such that smooth flow through receptacle (202) may be maintained. See also FIG. 2a, which shows the lower contour (115) of valve (114), having a slightly shorter wavelength than that of the second embodiment shown in FIG. 5a, but also avoids collection of fluid thereat.

Additionally, as seen in FIG. 6a, in the second embodiment of sampling port (200), flange (229) of valve (214) is sandwiched between disc (221) of securing member (220) and lip (240) of receptacle (202), for positioning valve (214) above and aligned with valve separator (210). This arrangement of the second embodiment is in contrast to the arrangement of the first embodiment of sampling port (100) (see FIG. 2a) in which valve (114) is maintained in position by lip (122) and neck (132) disposed in grooves (124) and (138) respectively, as described herein above.

An alternative aspect of the receptacle (302) of a fluid sampling port of the present invention is shown in FIG. 8 in an isometric view, with valve separator (310) extending from bottom surface (312), longitudinally oriented orthogonal to the direction of fluid flow through receptacle (302). This is in contrast to the first and second embodiments in which the valve separator is longitudinally oriented in the direction of fluid flow through the receptacle.

In the first and second embodiments, the sampling port would be useful mainly for sampling during a dialysis procedure because the valve separator provides minimal obstruction to the fluid flow. However, the alternative aspect of the sampling port is preferably for arterial line use. Due to the orientation of valve separator (310), significant obstruction of fluid flow through receptacle (302) may occur. This can assist in "cleaning" the area below the valve after sampling.

With reference to FIG. 9 showing a partially cut isometric view of an assembled sampling port (300) having the alternative aspect of valve separator (310), with a luer connector (344) mated therewith, slit (316) of valve (314) is seen oriented orthogonal to the longitudinal orientation of valve separator (310) in order to form a gap (348), (350) between each end of separated slit (316) and the narrow middle section (313) of valve separator (310) as described herein above regarding the first embodiment.

Although FIG. 9 shows the fluid sampling port (300) with the alternative aspect of valve separator (310), and having essentially the same components as that of the first embodiment, it is understood that a sampling port having essentially the same components as that of the second embodiment may contain the alternative aspect of the valve separator (310) as well.

It should be noted that in all embodiments of the present invention the valve comprises a shore hardness that is determined depending on the application of the fluid sampling port. For instance, when used for arterial line sampling the shore hardness is chosen in order to avoid "dumping" of blood pressure. When used for dialysis the shore hardness is chosen such that the valve slit will not be affected, and opened due to the vacuum generated by the dialysis machine.

It is understood that the above description of the embodiments of the present invention are for illustrative purposes only, and is not meant to be exhaustive or to limit the invention to the precise form or forms disclosed, as many modifications and variations are possible. Such modifications and variations are intended to be included within the scope of the present invention as defined by the accompanying claims.

The invention claimed is:

1. A fluid sampling port for a housing through which fluid flows, the housing having an inlet and outlet defined in opposite sides to establish an elongated flow path through the housing with the housing defining an opening communicating with the flow path through the housing, the sampling port comprising; a cylindrical resilient valve body having a normally closed, through, axial slit defining at least two slit segments, the cylindrical resilient valve body including an upper portion with a top surface, a lower portion with a bottom flange that is sized to rest on said housing surrounding and closing the opening in said housing, and a shoulder defined between the upper portion and the lower portion; and a planar disc securing member defining a central opening, the planar disc securing member including a planar disc portion, and an upstanding rim above the planar disc portion and surrounding the central opening, the planar disc securing member being mounted in registry with the opening in the housing, wherein said resilient valve body is inserted into the central opening of the planar disc securing member with the upper portion of the resilient valve body above the planar securing member, with the upstanding rim of the planar disc securing member bearing against the shoulder between the upper portion and the lower portion of the resilient valve body, and with the bottom flange and lower portion of the resilient valve body below the planar disc portion of the planar disc securing member, said planar disc securing member clamps the bottom flange of the resilient valve body to the housing and seals the opening in the housing, with the upper portion of the resilient valve body protruding upwardly through the central opening in the planar disc securing member, and the normally closed slit of the resilient valve body is capable of receiving a needleless connector so as to stress the slit segments of the resilient valve body and force these slit segments into the housing to establish a gap for withdrawal of a fluid sample.

2. The fluid sampling port according to claim 1, further comprising a cylindrical securing member that surrounds the upper portion of the resilient valve body, and defines a cylindrical band that engages the upper portion of the resilient valve body, an upper end of the cylindrical securing member having a bent-in rim that engages the top surface of the upper portion of the resilient valve body so as to clamp the upper portion of the resilient valve body.

3. The fluid sampling port according to claim 2, wherein the cylindrical securing member is externally threaded for mating with a needle-less connector.

4. The fluid sampling port according to claim 2, wherein the resilient valve body defines a groove in the top surface of the upper portion of the resilient valve body, the bent-in rim of the cylindrical securing member engaging in the groove.

5. The fluid sampling port according to claim 1, wherein a bottom surface of the bottom flange of the resilient valve body has a contour that is shaped as the crest of a wave whose length is greater than amplitude.

6. The fluid sampling port according to claim 1,
wherein the housing defines a shelf surrounding the opening communicating with the flow path through the housing,
the bottom flange of the resilient valve body is positioned on said shelf, and
the planar disc portion of the planar disc securing member comprises a rigid disc having a peripheral downward rim that surrounds and clamps the bottom flange to the shelf.

7. The fluid sampling port according to claim 1, further comprising: a cylindrical securing member, wherein the planar disc securing member clamps the lower portion of the resilient valve body with the housing, and the cylindrical securing member clamps the upper portion of the resilient valve body, such that the resilient valve body is clamped at both the upper portion and the lower portion of the resilient valve body.

8. The fluid sampling port according to claim 1, further comprising a male luer, the male luer serving as the needleless connector and being received in the slit of the resilient valve body so as to force the slit segments of the resilient valve body into the housing to establish the gap for withdrawal of the fluid sample.

9. The fluid sampling port according to claim 1, wherein the bottom flange of said resilient valve body that rests on said housing surrounding the opening in said housing is peripherally notched so that a lower portion of the bottom flange fits into the opening.

10. The fluid sampling port according to claim 1, further including an elongated profiled projection fixed on an inside surface of the housing in an alignment with the resilient valve body and positioned in the flow path through the housing for contacting the fluid above a bottom of the flow path.

11. The fluid sampling port according to claim 1, further comprising:
an elongated profiled projection fixed on an inside surface of the housing in an alignment with the resilient valve body and positioned in the flow path through the housing,
wherein the slit segments of the resilient valve body can be forced to engage the elongated profiled projection so as to establish the gap for withdrawal of the fluid sample.

12. A fluid sampling port for a housing through which fluid flows, the housing having an inlet and outlet defined in opposite sides to establish an elongated flow path through the housing with the housing defining an opening communicating with the flow path through the housing, the sampling port comprising:
a cylindrical resilient valve body having a normally closed, through, axial slit defining at least two slit segments, the cylindrical resilient valve body including an upper portion, a lower portion with a bottom flange that is sized to rest on the housing surrounding and closing the opening in the housing, and a shoulder defined between the upper portion and the lower portion;
a planar disc securing member defining a central opening, the planar disc securing member including a planar disc portion, and an upstanding rim above the planar disc portion and surrounding the central opening; and
an elongated profiled projection fixed on an inside surface of the housing in an alignment with the resilient valve body and positioned in the flow path through the housing,
wherein the upper portion of the resilient valve body is above the planar securing member, the upstanding rim of the planar disc securing member bears against the shoulder of the resilient valve body, and the bottom flange of the resilient valve body is below the planar disc portion of the planar disc securing member,
the planar disc securing member clamps the bottom flange of the resilient valve body to the housing and seals the opening in the housing, with the upper portion of the resilient valve body protruding upwardly through the central opening in the planar disc securing member, and
the normally closed slit of the resilient valve body is capable of receiving a needleless connector so as to stress the slit segments of the resilient valve body and force these slit segments to engage the elongated profiled projection so as to establish a gap for withdrawal of a fluid sample.

13. The fluid sampling port according to claim 12, further comprising a cylindrical securing member that surrounds the upper portion of the resilient valve body and defines a cylindrical band that engages the upper portion of the resilient valve body, an upper end of the cylindrical securing member having a bent-in rim that engages a top surface of the upper portion of the resilient valve body so as to clamp the upper portion of the resilient valve body.

14. The fluid sampling port according to claim 13, wherein the elongated profiled projection has a central portion that is narrower than end portions of the elongated profiled projection.

15. The fluid sampling port according to claim 13, wherein the elongated profiled projection has a figure-eight cross-sectional shape when cut longitudinally, planar with a bottom surface of the housing.

16. The fluid sampling port according to claim 13, wherein the elongated profiled projection is longitudinally aligned with the flow path through the housing.

17. The fluid sampling port according to claim 13, wherein the elongated profiled projection transversely extends across the flow path through the housing.

18. The fluid sampling port according to claim 13, wherein the slit in the resilient valve body is aligned orthogonal to a longitudinal axis of the elongated profiled projection.

19. The fluid sampling port according to claim 13, wherein the slit in the resilient valve body is longitudinally aligned with the elongated profiled projection.

* * * * *